United States Patent
Cazin et al.

(10) Patent No.: US 10,128,447 B2
(45) Date of Patent: Nov. 13, 2018

(54) LUMINESCENT PALLADIUM(0) AND PLATINUM(0) CARBENE COMPLEXES FOR OLEDS

(71) Applicant: UNIVERSITY COURT OF THE UNIVERSITY OF ST ANDREWS, St Andrews (GB)

(72) Inventors: Catherine Cazin, Fife (GB); Ifor David William Samuel, Fife (GB); Eli Zysman-Colman, Fife (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 0 days.

(21) Appl. No.: 15/532,298

(22) PCT Filed: Dec. 1, 2015

(86) PCT No.: PCT/GB2015/053670
§ 371 (c)(1),
(2) Date: Jun. 1, 2017

(87) PCT Pub. No.: WO2016/087844
PCT Pub. Date: Jun. 9, 2016

(65) Prior Publication Data
US 2018/0212160 A1    Jul. 26, 2018

(30) Foreign Application Priority Data

Dec. 2, 2014 (GB) .................................. 1421390.4

(51) Int. Cl.
| | |
|---|---|
| *H01L 51/00* | (2006.01) |
| *C09K 11/06* | (2006.01) |
| *C07F 15/00* | (2006.01) |
| *H01L 51/50* | (2006.01) |

(52) U.S. Cl.
CPC ........ *H01L 51/0084* (2013.01); *C07F 15/006* (2013.01); *C09K 11/06* (2013.01); *H01L 51/0087* (2013.01); C09K 2211/1007 (2013.01); *C09K 2211/1044* (2013.01); *C09K 2211/185* (2013.01); *H01L 51/5016* (2013.01); *H01L 51/5032* (2013.01)

(58) Field of Classification Search
CPC ........................ H01L 51/0084; H01L 51/0087
See application file for complete search history.

(56) References Cited

U.S. PATENT DOCUMENTS

2005/0260444 A1   11/2005 Forrest et al.
2015/0073152 A1   3/2015 Bold et al.

FOREIGN PATENT DOCUMENTS

JP   2010171155 A   8/2010

OTHER PUBLICATIONS

Tsubomura Taro et al. "Luminescent palladium(0) complexes bearing N-heterocyclic carbene and phosphine ligands", Inorganic Chemistry Communications, vol. 35, pp. 110-112.
Adam F. Henwood et al. "Palladium(0) NHC complexes: a new avenue to highly efficient phosphorescence", Chemical Science, vol. 6, No. 5, Jan. 1, 2015, pp. 3248-3261, UK.
WIPO; International Search Report and Written Opinion for International Application No. PCT/GB2015/053670, dated Feb. 15, 2016, 9 pages.
UKIPO; Search Report for British Application No. GB1421390.4, dated Oct. 30, 2015, 4 pages.
Titcomb et al, "Unexpected reactivity of two-coordinate palladium-carbene complexes; synthetic and catalytic implications", ChemComm Communication, 2001, 2 pages.

*Primary Examiner* — Joseph R Kosack
(74) *Attorney, Agent, or Firm* — Christopher J. Knors; Moore & Van Allen PLLC (57) ABSTRACT

A light-emitting device includes an organometallic complex of the form Z-M-$Z^1$, as light emitting material. M is Pd(0) or Pt(0) and Z is a nitrogen containing heterocyclic carbene ligand. $Z^1$ is a phosphorus ligand or a nitrogen containing heterocyclic carbene ligand that may be the same as or different from Z. The light emitting device may be an organic light-emitting diode (OLED), a sensor, or a light-emitting electrochemical cell (LEEC).

26 Claims, 2 Drawing Sheets

LUMINESCENT PALLADIUM(0) AND PLATINUM(0) CARBENE COMPLEXES FOR OLEDS

CROSS-REFERENCE TO RELATED APPLICATIONS

This application is a 35 U.S.C. § 371 National Stage Application of International Application No. PCT/GB2015/053670, filed Dec. 1, 2015, which claims the benefit of British Application No. 1421390.4 filed on Dec. 2, 2014, the entirety of each of which is incorporated herein by reference.

FIELD OF THE INVENTION

The present invention relates to the provision of light emitting devices such as OLEDs and sensors comprising organometallic complexes of palladium and platinum.

BACKGROUND TO THE INVENTION

Transition metal complexes bearing nitrogen containing N-heterocyclic carbene (NHC) ligands or phosphine ligands have been widely studied for use in catalysis, medicinal and materials chemistry.

The luminescent properties of transition metal complexes of palladium(0) or platinum(0) bearing NHC, or NHC and phosphorus, ligands have not been studied extensively. In contrast the luminescent properties of Cu(I), Ir(III), Pt(II) and Au(I) complexes have been subject to consideration for use in light-emitting devices such as organic light emitting diodes (OLEDs) or for sensing applications such as sensing oxygen.

Some studies have been carried out on Pd(0) and Pt(0) tetra-coordinate complexes using bidentate aryl phosphine ligands (Inorg. Chem. 2008, 47, p481-486; Tsubomura et al). Palladium (0) complexes having two or three monodentate phosphine ligands coordinating to the metal have been studied (Inorganic Chemistry Communications 2012, 20, p27-29; Ohkubo et al). Relatively weak and very weak luminescence was found for the examples studied (in solution), respectively.

More recently some examples of two coordinate palladium (0) complexes bearing an NHC and a triaryl phosphine ligand have been studied (Inorganic Chemistry Communications 2013, 35, p110-112; Tsubomura et al). A low photoluminescence quantum yield (1.4%) emission was observed for the only complex measured in that study in toluene solution.

There remains the need to find new materials for light emitting devices and sensors.

DESCRIPTION OF THE INVENTION

According to a first aspect the present invention provides a light-emitting device comprising an organometallic complex of the form Z-M-Z$^1$ as light emitting material, wherein M is Pd(0) or Pt(0)

Z is a nitrogen containing heterocyclic carbene ligand; and

Z$^1$ is a phosphorous ligand selected from the group consisting of:

and wherein each group R$^1$, R$^2$, R$^3$ is independently selected from the group consisting of substituted or unsubstituted primary, secondary or tertiary alkyl, that may be cyclic and may be unsaturated; and optionally two or more of the groups R$^1$, R$^2$, R$^3$, when not bonded to phosphorus via oxygen, are fused to form a ring; or Z$^1$ is a nitrogen containing heterocyclic carbene ligand that may be the same as or different from Z.

According to another aspect, the present invention also provides the use of complexes of the form Z-M-Z$^1$ as luminescent materials.

The complexes of the form Z-M-Z$^1$ described herein can show bright emission with good photoluminescence quantum yield (PLQY), of the order of 10 to 70% for example. Lifetimes of the emissions can be of the order of 1 to 10 μs for example. This is highly suitable for light-emitting devices such as OLED displays. The transition responsible for the emission is thought to be a triplet charge transfer (M→NHC) rather than to phosphorus (where present).

Advantageously the light-emitting device may be an organic light emitting diode (OLED). Such a device may comprise; an anode, a cathode and an emissive layer between the anode and cathode, wherein the emissive layer comprises at least one organometallic complex of the form Z-M-Z$^1$ as described herein. In general light emitting devices may employ one or more organometallic complexes of the form Z-M-Z$^1$, optionally together with other materials, as an emissive layer.

The light-emitting device may be a sensor. The sensor can make use of the moderating effect of an analyte on the light-emitting behaviour of the organometallic complex of the form Z-M-Z$^1$. For example small molecules such as oxygen, hydrogen or solvents such as dichloromethane can interact with the complexes changing their luminescent behaviour. The interaction may be reversible or irreversible, depending on the analyte and the complex employed. The interaction with a small molecule analyte may result in a reduced or an increased output of light, a change in wavelength of emission, a change in lifetime of emission or some combination of these effects. These changes in behaviour of the light-emitting device may be detected by eye or detected and/or measured by a suitable detection device.

Other light emitting devices may be constructed, for example a light-emitting electrochemical cell (LEEC). Such a device may comprise; an anode, a cathode and an emissive layer between the anode and cathode, wherein the emissive layer comprises at least one organometallic complex of the form Z-M-Z$^1$ as described herein. The LEEC will also comprise a mobile ion source.

Where the complex Z-M-Z$^1$ includes Z$^1$ as a phosphorous ligand the groups R$^1$, R$^2$, and R$^3$ may conveniently be the same.

Where the complex Z-M-Z$^1$ includes Z$^1$ as an NHC then both NHC ligands may conveniently be the same.

Each group R$^1$, R$^2$, and R$^3$ may be cycloalkyl, for example cyclopentyl or cyclohexyl or substituted cyclopentyl or cyclohexyl. Each group R$^1$, R$^2$, and R$^3$ may be tertiary alkyl, or substituted tertiary alkyl. For example tertiary butyl ($^t$Bu) or substituted tertiary butyl.

Groups $R^1$, $R^2$, $R^3$ may be substituted, for example once, twice, or three times, e.g. once, i.e. formally replacing one or more hydrogen atoms of the alkyl group. Examples of such substituents are, independently for each occurrence, halo (e.g. fluoro, chloro, bromo and iodo), $SF_5$, $CF_3$, aryl, aryl hydroxy, nitro, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl, For example R may be substituted or unsubstituted C1-C20 or even C1-C10 alkyl, aryl or heteroaryl. Where substituents R on the nitrogen are alkyl, aryl or heteroaryl they may be saturated or unsaturated and if substituted may be substituted by the same substituents described for groups $R^1$, $R^2$ and $R^3$.

By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto. Where $R^1$, $R^2$ and $R^3$ are substituted by aryl they may be C5 or C6 aryl with one or more carbon atoms replaced, independently for each replacement, by O, N, or S.

The cyclohexyl or cyclopentyl groups if present may be saturated or unsaturated and may be substituted as described above.

The N-heterocyclic carbenes (NHCs) may be NHC ligands bearing one two or three nitrogen atoms in the carbene ring.

Where the NHC ligand has one nitrogen atom in the carbene ring it may have the form:

wherein the groups $R^4$, $R^5$, $R^6$, $R^7$ and $R^8$ may be the same or different for each occurrence. Each $R^4$, $R^5$, $R^6$, $R^7$ and $R^8$ may be, independently for each occurrence, selected from: H, a primary or secondary alkyl group (for example C1-C10 or even C1-C4) that may be substituted or unsubstituted, substituted or unsubstituted aryl or heteroaryl (for example substituted or unsubstituted phenyl, substituted or unsubstituted naphthyl, or substituted or unsubstituted anthracenyl), or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy; optionally $R^4$ and $R^5$ may be fused to form a cycloalkyl ring (for example C5 or C6) that may be substituted or unsubstituted. Where the NHC ligand has three nitrogen atoms in the carbene ring it may have the form:

wherein the groups $R^4$, $R^5$, $R^6$, and $R^8$ may be the same or different for each occurrence. Each $R^4$, $R^5$, $R^6$, and $R^8$ may be, independently for each occurrence, selected from: H, a primary or secondary alkyl group (for example C1-C10 or even C1-C4) that may be substituted or unsubstituted and may be unsaturated, substituted or unsubstituted aryl or heteroaryl (for example substituted or unsubstituted phenyl, substituted or unsubstituted naphthyl, or substituted or unsubstituted anthracenyl), or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy; optionally $R^4$ and $R^5$ may be fused to form a cycloalkyl ring (for example C5 or C6) that may be substituted or unsubstituted.

Where there are two or three nitrogen atoms in the ring of the NHC two nitrogen atoms may be adjacent to the carbene carbon i.e. the nitrogen containing heterocyclic carbene ligand Z has a nitrogen atom in the carbene ring at both positions adjacent to, at either side of, the carbene carbon.

Where there are two nitrogen atoms in the carbene ring, the NHC carbene ligands of this type may have the form:

A

B

C wherein each of the groups $R^4$, $R^5$, $R^6$, $R^7$ and $R^8$ may be the same or different for each occurrence and the dashed line in the ring of formula A represents optional unsaturation, wherein $R^7$ is absent. Each $R^4$, $R^5$, $R^6$, $R^7$ and $R^8$ may be, independently for each occurrence, selected from: H, a primary or secondary alkyl group (for example C1-C10 or even C1-C4) that may be substituted or unsubstituted and may be unsaturated, substituted or unsubstituted aryl or heteroaryl (for example substituted or unsubstituted phenyl, substituted or unsubstituted naphthyl, or substituted or unsubstituted anthracenyl), or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy.

Advantageously the groups $R^6$ and $R^8$ may be substituted or unsubstituted aryl or heteroaryl, for example substituted or unsubstituted phenyl Suitable examples of NHC carbene ligands include those according to formulas I to V below:

wherein each group $R^9$, $R^{10}$ and $R^{11}$, is independently for each occurrence selected from: H, a primary or secondary alkyl group (for example C1-C10 or even C1-C4) that may be substituted or unsubstituted and may be unsaturated, substituted or unsubstituted aryl or heteroaryl (for example, substituted or unsubstituted phenyl, substituted or unsubstituted naphthyl, or substituted or unsubstituted anthracenyl), or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —SF$_5$, CF$_3$, and silyloxy;

$R^{12}$, $R^{13}$, $R^{14}$, $R^{15}$, $R^{17}$ and $R^{18}$ are each independently for each occurrence H, a substituted or unsubstituted alkyl group (for example C1-C10 or even C1-C4), substituted or unsubstituted aryl or heteroaryl, or $R^{12}$ and $R^{14}$ together with the carbons carrying them form a substituted or unsubstituted, fused 4-8 membered carbocyclic ring or a substituted or unsubstituted, fused aromatic ring, preferably a fused phenyl ring; and $R^{16}$ is alkyl (for example C1-C10 or even C1-C4) or a cycloalkyl (for example C3-C8).

For example these NHC carbenes of formulas VI to VIII:

wherein each group $R^{11}$ is for each occurrence independently selected from the group consisting of , —SO$_2$R$^x$, —SF$_5$, —CF$_3$, —F, —Br, —Cl, —I, —OMe, —NR$^x{}_2$, —CN, —C(O)R$^x$, —CO$_2$R$^x$, —CONR$^x{}_2$, —OR$^x$ and —R$^x$, wherein each R$^x$ independently for each occurrence selected from —H, a primary or secondary alkyl group (for example C1-C10 or even C1-C4) that may be substituted or unsubstituted, substituted or unsubstituted aryl or heteroaryl (for example substituted or unsubstituted phenyl, substituted or unsubstituted naphthyl, or substituted or unsubstituted anthracenyl), or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —SF$_5$, CF$_3$, and silyloxy; each group $R^{12}$ and $R^{14}$ is independently for each occurrence selected from the group consisting of —H, —CN, —Cl, and —CF$_3$; each group $R^{12}$ and $R^{14}$ in formula VI have the same meaning as in formulas I to IV; and wherein each group $R^9$ is selected from the group consisting of: methyl, isopropyl, are examples of suitable NHC carbenes for use in the light emitting devices

In complexes of formulas VI, VII, VIIA or VIII, the groups $R^9$ may be the same for each occurrence. The groups $R^{11}$ may be the same for each occurrence. The groups $R^{12}$ and $R^{14}$ may be the same in formula VI, for example —H.

Where groups R ($R^4$ to $R^{18}$ or $R^x$) of the NHC carbene ligands described herein are optionally substituted they may be substituted, for example once, twice, or three times, e.g. once, i.e. formally replacing one or more hydrogen atoms. Examples of such substituents are, independently for each occurrence, halo (e.g. fluoro, chloro, bromo and iodo), $SF_5$, $CF_3$, aryl, heteroaryl, aryl hydroxy, heteroaryl hydroxyl, nitro, amino, alkoxy, alkylthio, carboxy, cyano, thio, formyl, ester, acyl, thioacyl, amido, sulfonamido, carbamate and the like. Where the optional substituent of a group is amino it may be $NH_2$, NHR or $NR_2$, where the substituents R on the nitrogen may be alkyl, aryl or heteroaryl (for example substituted or unsubstituted C1-C20 or even C1-C10). Cycloalkyl groups if present may be saturated or unsaturated and may be substituted as described above. By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto.

Examples of complexes of formulas VI and VII include:

IMes

SIMes

IPr where Cyoct is cyclooctyl.

A further alternative NHC ligand for the complexes is the following:

where two cyclododecyl ($C_{12}$) rings connecting spiro to the fused ring system are each represented by

DESCRIPTION OF SOME PREFERRED EMBODIMENTS AND EXPERIMENTAL RESULTS

Examples of complexes of the form Z-M-$Z^1$ were prepared in accordance with known procedures such as found in: A General Synthetic Route to Mixed NHC—Phosphane Palladium(0) Complexes (NHC=N-Heterocyclic Carbene), Serena Fantasia and Steven P. Nolan, Chem. Eur. J. 2008, 14, 6987-69, the entire contents of which are incorporated by reference in this application.

For example preparation of Pd(IPr*)(PCy$_3$) is illustrated in Scheme 1 below. This example shows the production of a complex of the form Z-M-$Z^1$ where Z is the NHC IPr* and $Z^1$ is tricyclohexylphosphine (—PCy$_3$).

A Schlenk tube was charged with [Pd(allyl)Cl(IPr*)] (0.175 mmol) and KOtBu (0.193 mmol) and iPrOH (3 mL). PCy$_3$ (0.175 mmol) was added. The reaction mixture was stirred during 2-6h. The solution was filtered and the solvent removed in vacuo.

[Pd(IPr*)(PCy$_3$)]

$^1$H NMR (300 MHz, C$_6$D$_6$, 298K): δ (ppm)=7.82 (d, $^3J_{HH}$=7.8 Hz, 8H), 7.29 (t, J=7.8 Hz, 8H), 7.14-7.03 (m, 9H), 7.00-6.90 (m, 19H), 6.20 (s, 4H), 5.27 (s, 2H), 2.20-2.10 (m, 6H), 1.98 (s, 9H), 1.99-1.70 (m, 7H), 1.66-1.52 (m, 7H), 1.38-1.23 (m, 7H), 1.15-0.99 (m, 4H).

$^{31}$P NMR (121 MHz, C$_6$D$_6$, 298K): δ (ppm)=44.4

Complexes where both Z and $Z^1$ of Z-M-$Z^1$ are NHC may, for example, be made by a similar route or by other known methods. Such synthesis is described for example in Chem. Eur. J. 2008, 14, 6987-69 discussed above. Platinum complexes may be prepared by similar routes to those used for palladium complexes.

Scheme 2 below shows examples of Z-M-$Z^1$ complexes 2 to 6 where M=Pd(0) and, as a comparative example, the complex [Pd(IPr)(PPh$_3$)] (1) whose luminescent properties are described in Inorg. Chem. Commun., (2013), 35, 110-112.

-continued (5) Z = IPr
Z¹ = IPr (6) Z = SIPr
Z¹ = SIPr

Test results for luminescence data of complexes 2 to 6 and the comparative example 1 are shown in Table 1 below. The data was obtained in toluene solution under an argon atmosphere, with an excitation wavelength of 360 nm.

TABLE 1

Luminescence data for complexes 1-6

| Complex Number | Complex | Emission (nm) | Stokes shift (cm$^{-1}$) | Life-time (μs) | Quantum yield Φ(%) |
|---|---|---|---|---|---|
| 1 | [Pd(IPr)(PPh$_3$)] (comparative example from prior art) | 512 | 4221 | 0.014 | 0.6 |
| 2 | [Pd(IPr)(PCy$_3$)] | 508 | 1546 | 1.56 | 18 |
| 3 | [Pd(SIPr)(PCy$_3$)] | 543 | 1950 | 5.46 | 57 |
| 4 | [Pd(IPr*)(PCy$_3$)] | 515 | 949 | 0.36 (15%), 1.59 (85%) | 11 |
| 5 | [Pd(IPr)$_2$] | 555 | 886 | 2.93 | 57 |
| 6 | [Pd(SIPr)$_2$] | 608 | 1346 | 5.62 | 62 |

Quantum yield determined using quinine sulfate as the standard (Φ$_{PL}$ = 54.6% in 0.5M H$_2$SO$_4$ at 298 K); Melhuish, W. H. *J. Phys. Chem.* 1961, 65, 229.

As can be seen from Table 1 comparative example 1 has a short emission lifetime and low quantum yield (0.6%) when compared with complexes 2 to 6 which have lifetimes of the order of 1 to 6 μs and a quantum yield for the emission of 11% to 62% in these examples. Therefore the examples of complexes where both groups Z and Z¹ are NHC or where Z is an NHC and Z¹ is a trialkyl phosphine (tricyclohexyl phosphine in these examples) show significantly enhanced emission characteristics.

Figure 1:
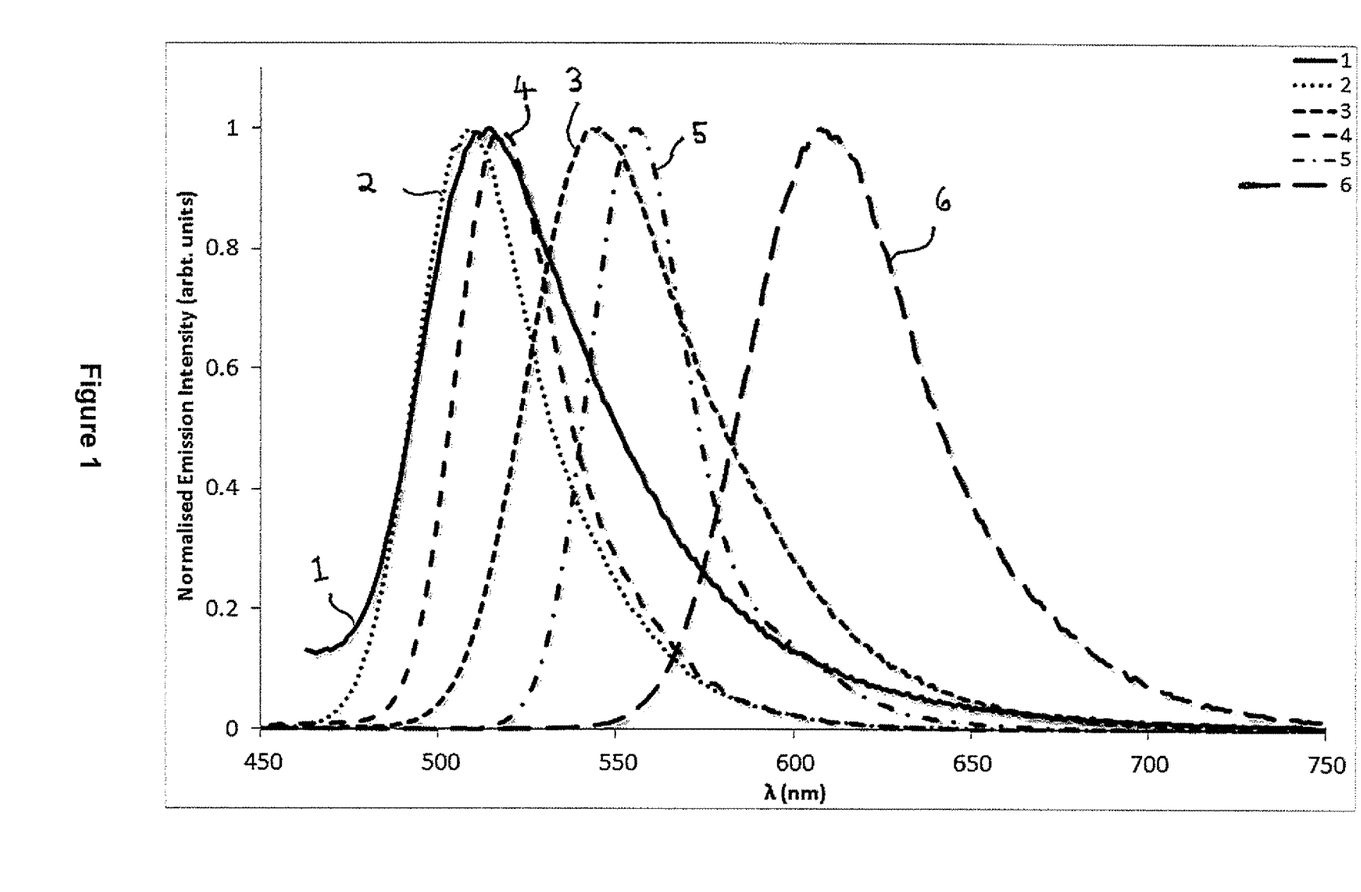
FIG. 1 shows normalised emission spectra for luminescent complexes.

FIG. 1 shows normalised emission spectra for the luminescent complexes 1 to 6.

The luminescence of complexes similar to the comparative example, complex 1, has been attributed to a triplet charge transfer (Pd→phosphine) excited state. For the complexes 2 to 6 where the phosphine does not have aromatic substituents (complexes 2 to 4) or where there is no phosphine present (complexes 5 and 6) the emission is thought to be derived from a triplet charge transfer (Pd→NHC) excited state.

An organic light-emitting diode was prepared on indium tin oxide (ITO) coated glass substrates of dimensions 12 mm×12 mm. The layer structure of the OLED is shown schematically in FIG. 2. The substrates were carefully cleaned by ultrasound in water, acetone and isopropanol for 15 minutes. All the organic layers on top of the ITO anode were prepared by spin coating inside a glovebox with oxygen and water content of less than 0.1 ppm. All the organic materials and solvents were used without further purification. All the solvents used were bought from Sigma Aldrich. The buffer layer poly(3,4-ethylenedioxythiophene) poly(styrenesulfonate) (PEDOT:PSS) was bought from Clevios and was used without further purification. Polymer poly (9-vinylcarbazole) (PVK) was bought from Sigma Aldrich and the organic small molecule 2,2',2''-(1,3,5-benzinetriyl)-tris(1-phenyl-1-H-benzimidazole) (TPBI) was bought from Luminescence Technology Corp. TPBI is also known as1,3,5-tris(N-phenylbenzimidizol-2-yl)benzene.

Figure 2:
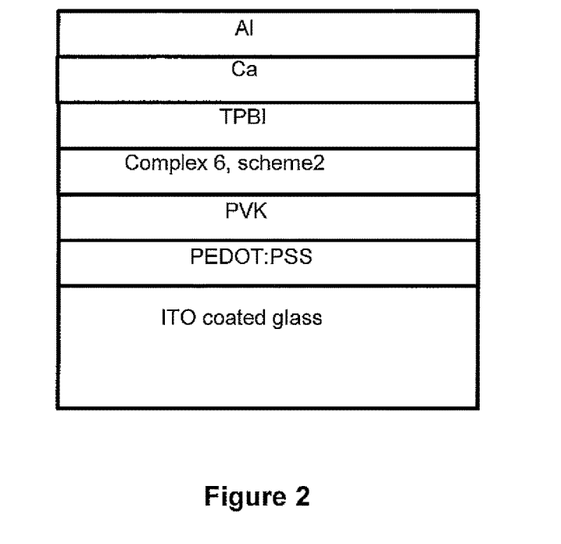
FIG. 2 shows, in schematic cross section, the layer structure of an OLED.

The organic light emitting diode structure was: ITO coated glass, a 40 nm layer of PEDOT: PSS deposited by spin coating at 4000 rpm for 60 seconds and baked on a hot plate at 120 ° C. for 15 minutes. A hole-transport layer of 35 nm-thick poly(N-vinylcarbazole) (PVK) was spin-coated on the PEDOT:PSS layer and baked at 80 ° C. for 2 hours in a nitrogen glove box. An emissive layer of complex 6, scheme 2 was spin coated on top of the PVK layer by spin-coating at 2000 rpm. An electron-transport layer of 60 nm-thick TPBI was deposited without a shadow mask in a thermal evaporator. A cathode of Ca/Al (20 nm/100 nm) was then deposited on the TPBI layer in the same vacuum system using a shadow mask to define the contact area and hence the pixel area. The concentration of polymer PVK in chlorobenzene was 10 mg/ml and of compound complex 6, scheme 2 was 5 mg/ml in degassed toluene solvent. The OLED consisted of three pixels of dimensions 2 mm×4 mm. The active area of the OLEDs was encapsulated by microscopic slides using UV curable epoxy (Norland 68) by shining 365 nm from a low power UV lamp for 3 minutes.

Figure 3:
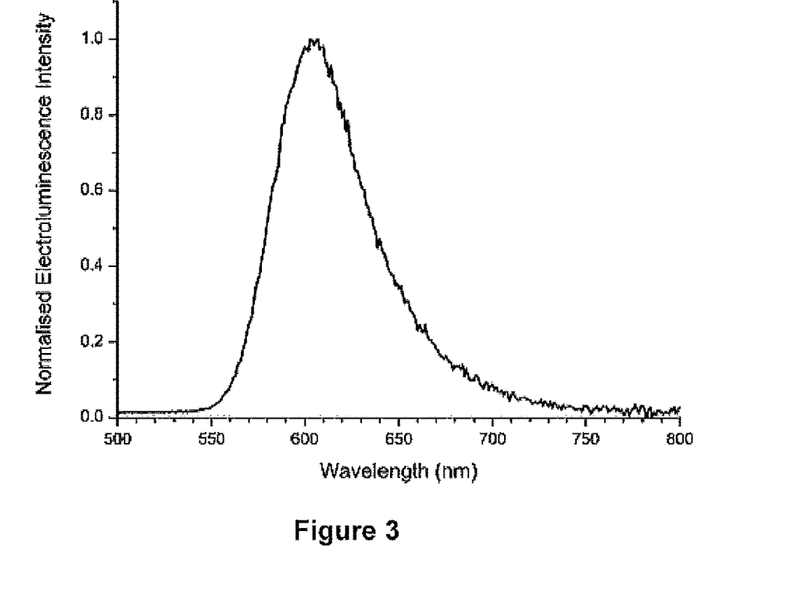
FIG. 3 shows the electroluminescence spectrum of an OLED.

When a voltage was applied, the device gave red light emission, and its electroluminescence spectrum (see FIG. 3) was measured for an applied voltage of 10 V using a charge coupled device spectrograph.

The invention claimed is:

1. A light-emitting device comprising an organometallic complex of the form Z-M-Z¹ as light emitting material, wherein:
   M is Pd(0) or Pt(0);
   Z is a nitrogen containing heterocyclic carbene ligand; and
   Z¹ is a phosphorus ligand selected from the group consisting of:

wherein each group $R^1$, $R^2$, $R^3$ is independently selected from the group consisting of substituted or unsubstituted primary, secondary or tertiary alkyl, that may be cyclic and may be unsaturated; and optionally two or more of the groups $R^1$, $R^2$, $R^3$, when not bonded to phosphorus via oxygen, are fused to form a ring; or $Z^1$ is a nitrogen containing heterocyclic carbene ligand that may be the same as or different from Z.

2. The light-emitting device of claim 1, wherein the said light-emitting device is an organic light-emitting diode.

3. The light-emitting device of claim 1, wherein the said light-emitting device is a sensor.

4. The light-emitting device of claim 1, wherein the said light emitting device is a light emitting electrochemical cell.

5. The light-emitting device of claim 1, wherein $Z^1$ is a phosphorus ligand and the groups $R^1$, $R^2$, $R^3$ are the same.

6. The light-emitting device of claim 1, wherein $Z^1$ is a phosphorus ligand and the groups $R^1$, $R^2$, $R^3$ are saturated or unsaturated cycloalkyl, that may be substituted.

7. The light-emitting device of claim 6, wherein $Z^1$ is a phosphorus ligand and the groups $R^1$, $R^2$, $R^3$ are independently for each occurrence selected from: saturated or unsaturated cyclopentyl or cyclohexyl, that may be substituted.

8. The light-emitting device of claim 1, wherein $Z^1$ is a phosphorus ligand and the groups $R^1$, $R^2$, $R^3$ are tertiary alkyl, that may be substituted.

9. The light-emitting device of claim 8, wherein $Z^1$ is a phosphorus ligand and the groups $R^1$, $R^2$, $R^3$ are tertiary butyl, that may be substituted.

10. The light-emitting device of claim 1, wherein nitrogen containing heterocyclic carbene ligand of Z has from one to three nitrogen atoms in the carbene ring.

11. The light-emitting device of claim 10, wherein the nitrogen containing heterocyclic carbene ligand Z has a nitrogen atom in the carbene ring at both positions adjacent to the carbene carbon.

12. The light-emitting device of claim 11, wherein the nitrogen containing heterocyclic carbene ligand Z has the form:

A or

B or

C wherein the dashed line in the ring of formula A represents optional unsaturation, wherein $R^7$ is absent; and wherein each $R^4$, $R^5$, $R^6$, $R^7$ and $R^8$ is, independently for each occurrence, selected from: H, a primary or secondary alkyl group that may be substituted or unsubstituted and may be unsaturated, substituted or unsubstituted aryl or heteroaryl or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —SF$_5$, CF$_3$, and silyloxy.

13. The light-emitting device of claim 12, wherein groups $R^6$ and $R^8$ are, independently for each occurrence, selected from substituted or unsubstituted aryl or heteroaryl.

14. The light-emitting device of claim 12, wherein the nitrogen containing heterocyclic carbene ligand Z is according to one of formulas I to V:

I

II

III

IV

-continued

V wherein each group $R^9$, $R^{10}$ and $R^{11}$, is independently for each occurrence selected from: H, a primary or secondary alkyl group that may be substituted or unsubstituted and may be unsaturated, substituted or unsubstituted aryl or heteroaryl, or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy; $R^{12}$, $R^{13}$, $R^{14}$, $R^{15}$, $R^{17}$ and $R^{18}$ are each independently for each occurrence H, a substituted or unsubstituted alkyl group, substituted or unsubstituted aryl or heteroaryl, or $R^{12}$ and $R^{14}$ together with the carbons carrying them form a substituted or unsubstituted, fused 4-8 membered carbocyclic ring or a substituted or unsubstituted, fused aromatic ring, preferably a fused phenyl ring; and $R^{16}$ is alkyl or a cycloalkyl.

15. The light-emitting device of claim 14, wherein the nitrogen containing heterocyclic carbene ligand Z is according to one of formulas VI to VIII:

VI

VII

VIIA

VIII wherein each group $R^{11}$ is for each occurrence independently selected from the group consisting of: —$SO_2R^x$, —$SF_5$, —$CF_3$, —F, —Br, —Cl, —I, —OMe, —$NR^x{}_2$, —CN, —C(O)$R^x$, —$CO_2R^x$, —$CONR^x{}_2$, —$OR^x$ and —$R^x$, wherein each $R^x$ is independently for each occurrence selected from —H, a primary or secondary alkyl group that may be substituted or unsubstituted, substituted or unsubstituted aryl or heteroaryl, or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy;

each group $R^{12}$ and $R^{14}$ is independently for each occurrence selected from the group consisting of —H, —CN, —Cl, and —$CF_3$;

each group $R^{12}$ and $R^{14}$ in formula VI are independently for each occurrence H, a substituted or unsubstituted alkyl group, substituted or unsubstituted aryl or heteroaryl, or $R^{12}$ and $R^{14}$ together with the carbons carrying them form a substituted or unsubstituted, fused 4-8 membered carbocyclic ring or a substituted or unsubstituted, fused aromatic ring, preferably a fused phenyl ring; and wherein each group $R^9$ is selected from the group consisting of: methyl, isopropyl, 16. The light-emitting device of claim 15, wherein the groups $R^9$ are the same for each occurrence.

17. The light-emitting device of claim 15, wherein the nitrogen containing heterocyclic carbene ligand Z is according to formula VI and the groups $R^{12}$ and $R^{14}$ are —H.

18. The light-emitting device of claim 11, wherein nitrogen containing heterocyclic carbene ligands of Z, are according to one of formulas:

IMes

SIMes wherein Cyoct is cyclooctyl.

19. The light-emitting device of claim 10, wherein the nitrogen containing heterocyclic carbene ligand Z has the form:

wherein each $R^4$, $R^5$, $R^6$, $R^7$ and $R^8$ is, independently for each occurrence, selected from: H, a primary or secondary alkyl group that may be substituted or unsubstituted, substituted or unsubstituted aryl or heteroaryl, or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy; and optionally $R^4$ and $R^5$ may be fused to form a cycloalkyl ring that may be substituted or unsubstituted.

20. The light-emitting device of claim 10, wherein the nitrogen containing heterocyclic carbene ligand Z has the form:

wherein each $R^4$, $R^5$, $R^6$, and $R^8$ is, independently for each occurrence, selected from: H, a primary or secondary alkyl group that may be substituted or unsubstituted and may be unsaturated, substituted or unsubstituted aryl or heteroaryl, or a functional group selected from the group consisting of halo, hydroxyl, sulfhydryl, cyano, cyanato, thiocyanato, acyl, alkoxy, amino, amido, arylsulphonyl, alkylsulphonyl, nitro, nitroso, sulfo, sulfonato, boryl, borono, phosphono, phosphonato, phosphinato, phospho, phosphino, —$SF_5$, $CF_3$, and silyloxy; and optionally $R^4$ and $R^5$ may be fused to form a cycloalkyl ring that may be substituted or unsubstituted.

21. The light-emitting device of claim 1, wherein $Z^1$ is a nitrogen containing heterocyclic carbene ligand that is the same as Z.

22. The light-emitting device of claim 1, wherein $Z^1$ is a nitrogen containing heterocyclic carbene ligand that is the different from Z and has from one to three nitrogen atoms in the carbene ring.

23. The light-emitting device of claim 1, wherein the organometallic complex of the form Z-M-$Z^1$ is selected from the group consisting of:

-continued wherein M is Pd(0) or Pt(0).

24. A method for generating light comprising:
providing an organometallic complex of the form Z-M-$Z^1$ as a luminescent material of a light emitting device, wherein
M is Pd(0) or Pt(0)
Z is a nitrogen containing heterocyclic carbene ligand; and
$Z^1$ is a phosphorus ligand selected from the group consisting of:

wherein each group $R^1$, $R^2$, $R^3$ is independently selected from the group consisting of substituted or unsubstituted primary, secondary or tertiary alkyl, that may be cyclic and may be unsaturated; and
optionally two or more of the groups $R^1$, $R^2$, $R^3$, when not bonded to phosphorus via oxygen, are fused to form a ring; or
$Z^1$ is a nitrogen containing heterocyclic carbene ligand that may be the same as or different from Z; and
operating the light emitting device such that light is produced at least in part from the organometallic complex.

25. The method of claim 24 wherein $Z^1$ is a nitrogen containing heterocyclic carbene ligand that is the same as Z.

26. The method of claim 24 wherein $Z^1$ is a nitrogen containing heterocyclic carbene ligand that is the different from Z and has from one to three nitrogen atoms in the carbene ring.

* * * * *

UNITED STATES PATENT AND TRADEMARK OFFICE
CERTIFICATE OF CORRECTION

PATENT NO. : 10,128,447 B2
APPLICATION NO. : 15/532298
DATED : November 13, 2018
INVENTOR(S) : Catherine Cazin, Ifor David William Samuel and Eli Zysman-Colman Page 1 of 1

It is certified that error appears in the above-identified patent and that said Letters Patent is hereby corrected as shown below:

In the Claims

Column 14, Claim 14, change Line 19 to:
ing to one of formulas I to V:

Column 16, Claim 15, change Line 1 to:
-SF$_5$, -CF$_3$, -F, -Br, -Cl, -I, -OMe, -NR$^x{}_2$, Column 16, Claim 15, change Line 18 to:
-Cl, and -CF$_3$;

Signed and Sealed this
Fifth Day of March, 2019

Andrei Iancu
*Director of the United States Patent and Trademark Office*